US011983876B2

(12) United States Patent
Nagaraj (10) Patent No.: US 11,983,876 B2
(45) Date of Patent: May 14, 2024

(54) IMAGE BASED DETECTION OF CHARACTERISTIC EYE MOVEMENTS

(71) Applicant: Siemens Healthcare GmbH, Erlangen (DE)

(72) Inventor: Nisarga Nagaraj, Bangalore (IN)

(73) Assignee: Siemens Healthineers AG, Erlangen (DE)

( * ) Notice: Subject to any disclaimer, the term of this patent is extended or adjusted under 35 U.S.C. 154(b) by 0 days.

(21) Appl. No.: 18/230,300

(22) Filed: Aug. 4, 2023

(65) Prior Publication Data
US 2024/0046475 A1  Feb. 8, 2024

(30) Foreign Application Priority Data
Aug. 5, 2022 (EP) .................................... 22189027

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/4863* (2013.01); *G06T 7/11* (2017.01);
(Continued)

(58) Field of Classification Search
CPC .................... G06T 7/0016; G06T 7/20; G06T 2207/30016; G06T 2207/30041
See application file for complete search history.

(56) References Cited

U.S. PATENT DOCUMENTS

2017/0039703 A1* 2/2017 Wang .................. A61B 5/4064
2019/0328231 A1* 10/2019 Song .................. G01R 33/5608
(Continued)

FOREIGN PATENT DOCUMENTS

| CN | 110415252 A | 11/2019 |
| CN | 113662659 A | 11/2021 |
| CN | 113744271 A | 12/2021 |

OTHER PUBLICATIONS

Rezatofighi, H. et al., "Generalized Intersection Over Union: A Metric and A Loss for Bounding Box Regression", Computer Science Department, Stanford University, United States School of Computer Science, The University of Ade-Iaide, Australia Aibee Inc, USA.
(Continued)

Primary Examiner — Molly Wilburn
(74) Attorney, Agent, or Firm — Banner & Witcoff Ltd.

(57) ABSTRACT

In a method for determining a type of characteristic eye movement of the eyes of a patient, the patient is provided with an optokinetic stimulus for the characteristic eye movement, a medical image of the brain of a patient also including the eyes of the patient is generated. An amount of a displacement of an optic nerve of the patient may be determined based on the medical image and a type of a characteristic eye movement may be determined based on the velocity of eye movement for the determined amount of displacement of the optic nerve. In a method for training an artificial intelligence based algorithm for determining an amount of a displacement of an optic nerve of a patient, the algorithm may be trained based on at least one medical image.

10 Claims, 7 Drawing Sheets

(51) Int. Cl.
 *G06T 7/11* (2017.01)
 *G06T 7/20* (2017.01)
(52) U.S. Cl.
 CPC ...... *G06T 7/20* (2013.01); *G06T 2207/20081* (2013.01); *G06T 2207/30016* (2013.01); *G06T 2207/30041* (2013.01)

(56) References Cited

U.S. PATENT DOCUMENTS

| 2022/0058796 A1 | 2/2022 | Vaghefi Rezaei | |
| 2022/0133145 A1* | 5/2022 | Franceschiello ... | G01R 33/4826 600/410 |

OTHER PUBLICATIONS

Redmon, Joseph et al.: "You Only Look Once: Unified, Real-Time Object Detection", in: CVPR, 2016, pp. 779-788.
Extended European search report—European Patent Application No. 22189027.0, dated Jan. 26, 2023.

* cited by examiner

| α [°] | t [s] | EM | IN | S |
|---|---|---|---|---|
| 30 | 1 | LEM | 100 | S1 |
| 30 | 0,8 | LBN | 100 | S2 |
| 30 | 1,5 | REM | 100 | S1 |
| 30 | 1 | RBN | 100 | S2 |
| 30 | 1,2 | UEM | 100 | S1 |
| 30 | 0,9 | UBN | 100 | S2 |
| 30 | 1 | DEM | 100 | S1 |
| 30 | 0,8 | DBN | 100 | S2 |

IMAGE BASED DETECTION OF CHARACTERISTIC EYE MOVEMENTS

CROSS REFERENCE TO RELATED APPLICATIONS

This patent application claims priority to European Patent Application No. 22189027.0, filed Aug. 5, 2022, which is incorporated herein by reference in its entirety.

BACKGROUND

Field

The disclosure relates to a method for determining a type of characteristic eye movement of a patient. The disclosure also concerns a method for training an artificial intelligence (AI)-based algorithm for determining an amount of a displacement of an optic nerve of a patient. Furthermore, the disclosure relates to an eye movement determination device. The disclosure also relates to a medical imaging system.

Related Art

Eye movement or oculomotor function is the term used to describe the movements of the bulbus oculi (eyeball) caused by the external eye muscles, which in humans are physiologically conjugated with the contralateral eye. In the type of eye following movement, a moving object is fixed. The eye follows the movements of the object by slow eye following movements. Saccades are rapid movements of the eye with a constant change of fixation point. Only the images from the time of fixation are perceived, the image shifts are suppressed. Nystagmus is the combination of saccades and eye following movements. The indication of the direction of the nystagmus depends on the rapid recoil movement. Knowledge of the brain structures responsible for eye movements makes it possible in many cases to recognize the underlying disease process or to localize the disease anatomically. Therefore, the examination of ocular motility is an important diagnostic procedure for many neurological and neuro-ophthalmological diseases.

Vestibular migraines as a type of neurological disease are a phenomenon which affects millions of people across the world. The term "migraine" is more or less familiar to everyone these days. Scientists assume that migraine symptoms are caused by a rapid drop in blood flow to the brain and the resulting change in activity in the affected brain regions. If the brain regions that belong to the vestibular system are affected, dizziness, and/or vertigo, can be the main symptom.

Attack-like permanent spinning or swaying dizziness occurs, which can last for minutes, hours—sometimes even several days. As with other types of migraine, some sufferers complain of increased sensitivity to light, noise or movement and therefore have an increased need for rest during the attack. In addition, there is often severe nausea as well as gait, balance and vision disorders. Headaches can occur before, during or after an attack, but are absent in good 30% of the cases. This often makes it difficult to distinguish it from the clinical picture of Meniere's disease, which causes similar symptoms.

Further, vestibular migraines may show symptoms that appear also in many other diseases. Hence, vestibular migraines are hard to diagnose and are not accurately diagnosed using the current methods that exist. Further, the time taken to declare that a patient has vestibular migraine is high and at times uncertain without conclusive evidence. Hence, sometimes, patients are put on clinical correlation on a trial basis for years to a lifetime.

Until today, in case a person suffers from vertigo, a magnetic resonance image of brain is normally generated, however the magnetic resonance image of brain is generated for ruling out disorders such as a tumor, epilepsy or multiple sclerosis. However, vestibular migraines are not detected based on a magnetic resonance image of brain. Hence, a diagnose of vestibular migraines is relatively uncertain. Therefore, a patient is merely put under clinical correlation and trial medicines, which may or may not help the patient, are applied to the patient.

Further, a test called video nystagmography, which is almost unheard of in many countries across the world, is used to detect the disorders causing vertigo. A video mask with an integrated camera is placed on the patient. With darkening (removal of the optical fixation), the movements of the pupils can be tracked automatically with an infrared camera and thus spontaneous or induced nystagmus can be recorded.

However, the reliability of such a test completely depends on the correlation experience or a technician conducting the test. Hence, it is not 100% accurate.

Thus, there is a problem of providing reliably measurement data of a patient used as a basis for unambiguously determining if the patient suffers from a certain neurological disease, in particular vestibular migraines, or not.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to solve the problems of the conventional solutions. These problems are solved by a method for determining a type of a characteristic eye movement of a patient according to one or more exemplary embodiments of the disclosure, by a method for training an AI-based algorithm for determining an amount of a displacement of an optic nerve of a patient according to one or more exemplary embodiments of the disclosure, by an eye movement determination device according to one or more exemplary embodiments of the disclosure, and by a medical imaging system according to one or more exemplary embodiments of the disclosure.

In an exemplary embodiment, the method for determining a type of eye movement of a patient, may include providing the patient with an optokinetic stimulus for a characteristic eye movement, preferably a nystagmus. Further, a medical image of the brain of a patient, also including the eyes of the patient, may be generated. A patient comprises a human person. In an exemplary embodiment, the medical image is recorded timed with the generation of the optokinetic stimulus, such that the medical image represents the reaction of the eyes of the patient to the optical stimulus. In an exemplary embodiment, the medical image is recorded simultaneously to the optical stimulation or directly or short after generation of the optical stimulus. As later described in detail, in an exemplary embodiment, "a medical image" may comprise exactly one medical image, more than one medical image, or a whole sequence of a plurality of medical images such that a kind of video sequence of the eyes of the patient is achieved.

In other words, in an exemplary embodiment, the medical image comprises a sectional internal view of the head of the patient. The view may be a sectional plane, a transversal plane relatively to the longitudinal axis of the body of the patient is used which is positioned at the height position of the eyes of the patient such that in addition to the brain, also a sectional view of the eyes including eyeballs and the optic nerves of the patient is shown. Hence, a medical image means an image of the interior of the head of the patient, preferably a sectional view, which also comprises a sectional depiction of the eyes of the patient. The medical image may include a plurality of such sectional views in different planes with the same or with different orientations such that a direction of the optic nerve in a two dimensional direction or even in a three dimensional direction can be derived from the medical image. Based on the medical image, an amount of a displacement of an optic nerve and velocity of the displacement of the optic nerve of the patient is determined.

An optokinetic stimulus comprises a video, which displays one or a plurality of moving objects for a patient, wherein the moving object exerts a movement stimulus to the eyes of the patient.

In an exemplary embodiment, it is then determined if the characteristic eye movement, preferably a nystagmus, is detected based on the determined amount of displacement of the optic nerve and preferably the velocity of displacement of the optic nerve. For a normal healthy patient, when optokinetic stimuli are shown, optic nerve displacement may not happen at all. In only happens if the healthy patient moves the eye intentionally. Normally, optokinetic stimuli do not have any effect on a healthy patient. The determination of the eye movement based on the optic nerve is highly deterministic since medical images of the optic nerve clearly record the optic nerve displacement. The displacement of the optic nerve and preferably the velocity of the displaced optic nerve can be measured by comparing a medical image recorded without optokinetic stimulation and a medical image recorded simultaneously with such an optokinetic stimulation. The velocity of displacement of the optic nerve is higher in patients with vestibular migraine. Since such medical images may be part of routine scans for example based on symptoms like vertigo, such a determination may reduce the turnaround time for a diagnosis of a neurological disease, in particular a diagnosis of vestibular migraine in case of the appearance of vertigo. Further, a perturbation of the patient by trial and error medicine can be avoided due to the reliable determination of the type of characteristic movement, in particular a nystagmus movement, of the eyes.

It has to be mentioned that there are a plurality of different neurological disorders that can be determined based on a characteristic eye movement. For example, in the case of the slow following eye movements, one checks whether these are smooth or saccadic. The latter speaks for central oculomotor dysfunction. A slightly sacced vertical downward gaze is also often found in healthy subjects. Physiological visual fixation suppression of the vestibular-ocular reflex is also an important test and is impaired in central cerebellar lesions.

Attention should be paid to the speed and accuracy of the saccades and to whether both eyes move in parallel. Hypermetric saccades are found in cerebellar disorders, hypometric saccades mostly in brainstem lesions and neuro-degenerative diseases. In the case of progressive supranuclear gaze palsy—an important differential diagnosis for idiopathic Parkinson's syndrome—there is usually initially a slowing down of the vertical saccades, then in the course of the disease also the horizontal saccades and finally a general gaze palsy.

In an exemplary embodiment, the eye movement determination device according to the disclosure may include a stimulation unit for providing the patient with an optokinetic stimulus for a predetermined type of characteristic eye movement, preferably a nystagmus. Further, the eye movement determination device comprises an image interface unit for receiving a medical image of the brain and the eyes of a patient from a medical imaging system or a scan unit of a medical imaging system. A part of the eye movement determination device is also a displacement determination unit for determining an amount of a displacement of the optic nerve(s) and velocity of the displacement of the optic nerve(s) of the patient based on the medical image and an analysis unit for determining if the predetermined characteristic eye movement, preferably a nystagmus movement, is detected based on the determined amount of displacement of the optic nerve(s) and the velocity of the displaced optic nerve(s) of the patient. The eye movement determination device shares the advantages of the method for determining a type of an eye movement of a patient.

In an exemplary embodiment, the medical imaging system according to the disclosure may include a scan unit (scanner) for acquiring medical imaging data from a patient and an eye movement determination device according to the disclosure. The medical imaging system shares the advantages of the eye movement determination device according to the disclosure and the method for determining a type of an eye movement of a patient according to the disclosure.

Some units or modules of the eye movement determination device mentioned above can be completely or partially realized as software modules running on a processor of a respective computing system, e.g. of a control device of a medical imaging system. A realization largely in the form of software modules can have the advantage that applications already installed on an existing computing system can be updated, with relatively little effort, to install and run these units of the present application. The object of the disclosure is also achieved by a computer program product with a computer program that is directly loadable into the memory of a computing system, and which comprises program units to perform the steps of the inventive method, at least those steps that could be executed by a computer, especially the steps of determining an amount of a displacement of the optic nerve and velocity of the displacement of the optic nerve of the patient based on the medical image and determining if a characteristic eye movement, preferably a nystagmus movement, is detected based on the determined amount of displacement of the optic nerve and the velocity of the displacement of the optic nerve, when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or their equivalents.

In an exemplary embodiment, the medical image or the medical images are recorded using a magnetic resonance imaging system. As mentioned above, in case a person suffers from vertigo, a magnetic resonance image of brain is normally generated, wherein the magnetic resonance image of brain is generated for ruling out disorders such as a tumor, epilepsy or multiple sclerosis. In an exemplary embodiment, the method according to the disclosure can advantageously be combined with such a routine medical imaging. Hence, in an exemplary embodiment, the medical image comprises a magnetic resonance image or even a sequence of magnetic resonance images. Advantageously, such magnetic resonance images, which are recorded for ruling out the above-mentioned severe disorders, can be additionally used for detecting and identifying a type of a characteristic eye movement to find out, in case the above-mentioned severe diseases are ruled out, from which disease the patient suffers indeed. Hence, there is no need for additional separate examinations and time and medical resources can be saved. In an exemplary embodiment, the magnetic resonance images are recorded using a dynamic sequence, in particular a Cine sequence. Advantageously, a movement of the eyes of a patient can be easily recorded.

In case the routine medical image of the brain is without any noticeable finding, the method for determining a type of characteristic eye movement of a patient, wherein an optic nerve displacement is detected using an optokinetic stimulus can be performed afterwards according to a new routine protocol and based on a new sequence. As later discussed, in an exemplary embodiment, for detecting and identifying a special type of a characteristic eye movement, a dynamic medical imaging method and in particular a dynamic magnetic resonance imaging method may be used. In case a magnetic resonance imaging method is used, which is advantageous due to an absence of radiation, a Cine sequence may be used. Such a dynamic magnetic resonance imaging method, in particular a Cine sequence, including a plurality of subsequently recorded frames, enables a real time recording of movements of internal organs of a patient, in particular the optic nerves of the eyes of a patient. Advantageously, also a time stamp of all the recorded frames is determined such that an exact place-time behavior of the optic nerves of a patient can be recorded.

Hence, in the method according to the disclosure, the medical image comprises a series or sequence of medical images. Advantageously, a movement of the eyes of the patent can be recorded and compared with predetermined movement patterns for determining a characteristic eye movement. Based on the characteristic eye movement, a specific neurological disease can be determined.

In an exemplary embodiment, in the method according to the disclosure, the optokinetic stimulus comprises a movement of an object in a predetermined direction. The predetermined direction of the movement of the object comprises at least one of:

a movement from left to right,
a movement from right to left,
a movement up and down,
a rotatory motion.

Advantageously, different movement patterns can be stimulated by the optokinetic stimulus. Optokinetic stimuli comprise many patterns which trigger nystagmus. This could be horizontal (left or right) or vertical (up or down). Hence, it is important to show all sorts of patterns in optokinetic stimuli because we do not know what kind of nystagmus a patient with a specific disease, in particular vestibular migraines, can get.

In an exemplary embodiment, the optokinetic stimulus comprises a video image of a distorted moving chessboard. Advantageously, such a moving pattern stimulates eye movements, in particular nystagmus movements of the eyes. Such a nystagmus comprises at least one of horizontal (left or right movement), vertical (up or down movement) or rotatory movements.

In an exemplary embodiment, the step of determining an amount of a displacement of the optic nerve comprises an AI-based determination (AI=artificial intelligence). Advantageously, such an AI-based determination of a quantity of a displacement of the optic nerve enables to avoid an error prone and non-deterministic manual determination by a radiologist, which can often lead to a misdiagnosis, because a patient can move his/her eyes during the display of the optokinetic stimulus. For generating an AI-based determination of an amount of displacement of the optic nerve, an AI model or algorithm is created and trained to detect a specific type of an eye displacement or even movement which is characteristic for a special neurological phenomenon, in particular a special neurological disease. As later described in detail, in an exemplary embodiment, such a type of characteristic eye movement comprises a type of nystagmus. Such a nystagmus may include at least one of the following types:
- a left beating nystagmus,
- a right beating nystagmus,
- an up beating nystagmus,
- a down beating nystagmus.

All these nystagmus movements may be indications of a vestibular migraine. If patient sees optokinetic stimuli and gets a nystagmus, then it means patient has vestibular migraines. Now that nystagmus can be anything, for example left horizontal or right horizontal or up vertical or down vertical.

The method for training an AI-based algorithm for determining an amount of a displacement of an optic nerve of a patient based on at least one medical image, comprises the steps of receiving labelled medical image data. The corresponding time stamp of these medical images are also recorded. With the amount of displacement of optic nerve and the time stamps of medical images, velocity of displayed optic nerve is calculated through the formula velocity equals distance divided by time. This velocity will be higher for patients with vestibular migraines.

For training an artificial intelligence model, as labelled medical image data a dataset with two different sets of medical images is needed: a first training set with medical images related to a patient with regular eye movement and a second training set with medical images of patients with the type of characteristic eye movement to be detected. As mentioned-above, such a characteristic eye movement may be related to a special type of neurological disease, in particular a vestibular migraine.

For generating labelled training data, each training medical image is manually provided with a bounding box which marks the location of the optic nerve. Further a simple text is added giving the classification of the marked object, in this case the optic nerve, as well as the coordinates and the size of its bounding box. The more medical images the training data set contains, the more effective the training will be. The accuracy of the training can be tested by providing a labelled test dataset. The outcome of this test is a score called mean average precision, which ranges from 0 to 1 (i.e. 0 to 100%).

After the training is completed and a high enough mean average precision score has been achieved, the output is a trained model or algorithm, which can be delivered to the eye movement determination device and be used to detect live data. A mean average precision score nearing 1 will allow for reliant and accurate localization of the optic nerve, thus providing accurate diagnosis.

In an exemplary embodiment, the detection of the optic nerve is realized by using a "You Only Look Once"-algorithm (by short YOLO-algorithm). Such a YOLO-algorithm is a performant algorithm allowing for real time analysis of the medical image. A YOLO-algorithm is described in Joseph Redmon, Santosh Divvala, Ross Girshick, Ali Fahrhadi, "You Only Look Once: unified, Real-time Object Detection", University of Washington, Allen Institute for AI, Facebook AI Research. The YOLO-algorithm is useful to analyze a high quantity of images. As above-mentioned, in case a whole sequence of images is analyzed and a pathologic neurological phenomenon exists, in particular vestibular migraine, each frame or image of such a sequence of images contains a differently localized part of the optic nerve compared to a localization of an optic nerve related to a normal or regular eye movement. Advantageously, a YOLO-algorithm is a performant algorithm to detect the optic nerve reliably and quickly such that it allows for real time analysis of the medical image(s).

In an exemplary embodiment, in an analogue manner to the above-mentioned step in the training of the method according to the disclosure, the step of AI-based determining an amount of a displacement of the optic nerve comprises the sub-step of segmenting the optic nerve in the medical image. As later described in detail, in an exemplary embodiment, identification, localization and segmentation of the optic nerve is achieved using the above-mentioned YOLO-algorithm.

In an exemplary embodiment, the sub-step of segmenting the optic nerve comprises the following steps:
- splitting the medical image into a grid including a plurality of cells,
- detecting the most likely object within each cell of the grid,
- marking each cell in which the optic nerve is detected by a bounding box,
- using of "Intersection over Union" for creating a unified single bounding box of the detected optic nerve.

In an exemplary embodiment, the medical image is split into a grid of equal dimension, typically in a grid of 7*7 rectangle cells. For each cell, the detection of the most likely object within each cell includes the determination if there is a part of an optic nerve.

For each cell which contains an optic nerve or a part of the optic nerve a bounding box, predicting the borders of the optic nerve, is generated. That process results in multiple bounding boxes surrounding different portions of the complete area of the optic nerve.

For providing just one single bounding box for one single optic nerve, a unification process is used, which may be based on "Intersection over Union". With a "single bounding box" one overall bounding box for one single optic nerve is meant. Intersection over Union (IoU by short), also named Jaccard index or Jaccard similarity coefficient, is a metric that allows us to evaluate how similar our predicted bounding box is to the ground truth bounding box. The idea is that we want to compare the ratio of the area where the two bounding boxes overlap to the total combined area of the two boxes. Principles of "Intersection over Union" and also a generalized version is described in Hamid Rezatofighi et al. "Generalized Intersection over Union: A Metric and A Loss for Bounding Box Regression", Computer Science Department, Stanford University, United States School of Computer Science, The University of Adelaide, Australia Aibee Inc, USA.

The score related to Intersection over Union results from dividing the area of overlap between the ground truth bounding box and the predicted bounding box through the area of union.

Each grid cell gives a prediction of its bounding box together with the confidence score. Confidence score is one parameter for the IoU calculation. In case the confidence score is equal to 1, the bounding box represents the real overall bounding box. This mechanism eliminates bounding boxes that are not equal to the real bounding box of an optic nerve. Hence, we get a final detection result as a bounding box for each detected optic nerve. That bounding box is also assigned to attributes such as the dimension and the position of the center of the bounding box. The dimension in particular comprises values related to the height and the width of the bounding box.

In an exemplary embodiment, an angle of the orientation of the detected optic nerve is calculated based on the height and width of the bounding box and the amount of a displacement of the optic nerve is determined based on the calculated angle. Using the diagonal of the bounding box as hypotenuse of a right angled triangle comprising the width and the height of the bounding box, the hypotenuse can be calculated based on the height and the width of the bounding box based on Pythagorean theorem. Then the angle α can be calculated as:

$$\alpha = \arccos(\text{height}/\text{hypotenuse}) \text{ or}$$

$$\alpha = \arcsin(\text{width}/\text{hypotenuse}).$$

In the method according to an exemplary embodiment of the disclosure, a series of medical images is generated and a velocity of an eye movement is determined based on the amount of displacement and a time stamp of each of the medical images. Further, the eye movement pattern, preferably a nystagmus, is detected based on the determined velocity. If the angle α is calculated for each frame of the recorded medical images, a live tracking is enabled on how and how fast the optic nerve has moved during the medical imaging under various situations. Based on the time stamps, it is well known for an accuracy of milliseconds, when these medical images have been taken. Hence, also a velocity of the recorded eye movement is determined. Such a velocity of the recorded eye movement can be compared with reference values for determining if an eye movement has been recorded which is characteristic for a specific physiologic condition of the patient.

In particular, if a nystagmus is detected and the velocity is greater than the velocity captured during a regular eye movement, then it is determined that the patient is considered to experience vertigo based on an optical stimulus. Such a physiological condition may be used for finding that the patient suffers from vestibular migraines. Hence, based on a sequence of medical images, preferably magnetic resonance images, it is enabled to find out if a patient suffers from a neurologic disease, in particular vestibular migraines.

Figure 1:
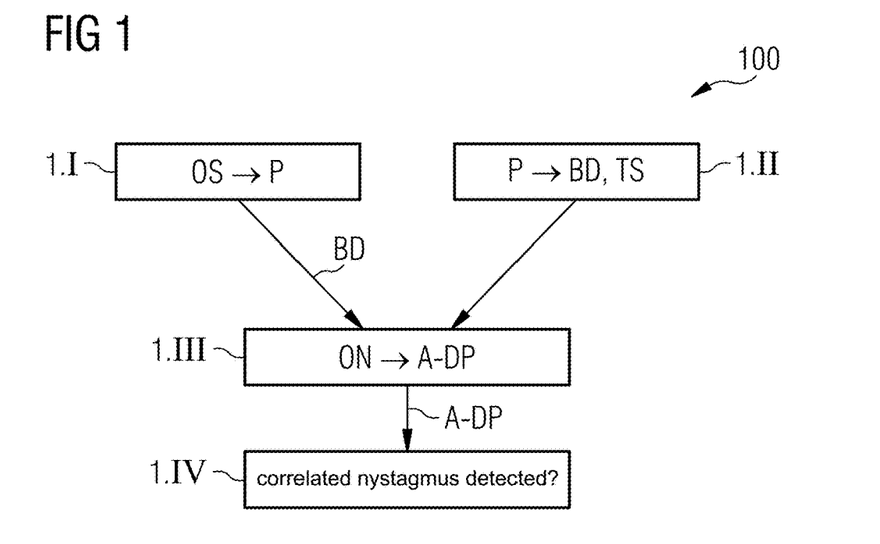
FIG. 1 shows a flowchart diagram illustrating the method for determining a type of a characteristic eye movement of a patient according to an exemplary embodiment of the disclosure.

In FIG. 1, a flow chart diagram 100 illustrating the method for determining a type of a characteristic eye movement of a patient P according to an embodiment of the disclosure, is shown.

Figure 5:
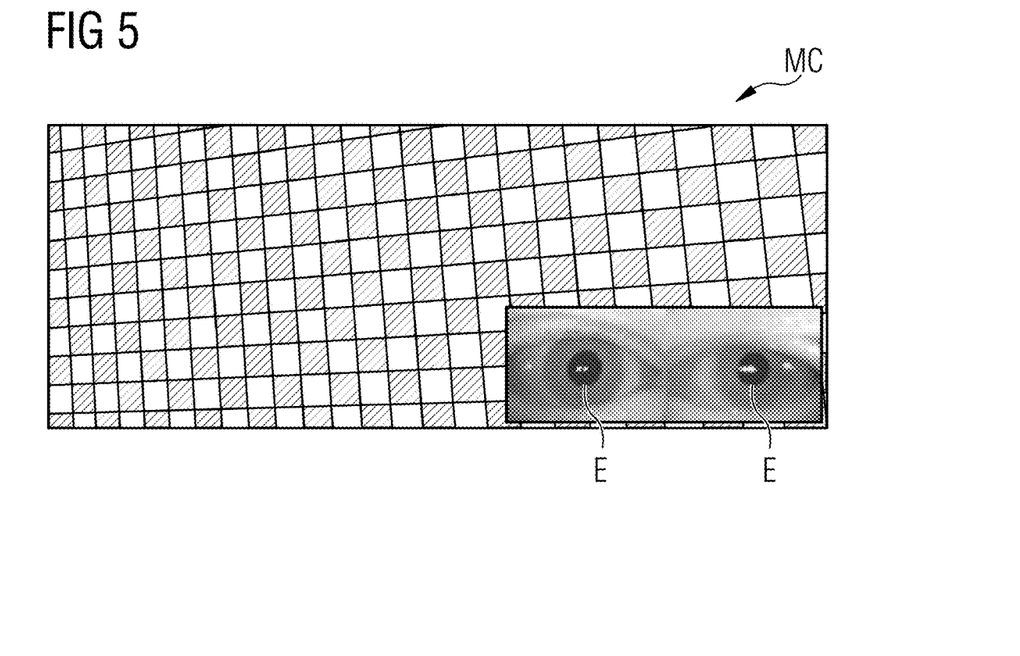
FIG. 5 shows a moving chessboard used as optokinetic stimulus for the eyes of a patient, according to an exemplary embodiment of the disclosure.

In step 1.I, an optokinetic stimulus OS for a nystagmus is shown to the patient P. Such an optokinetic stimulus OS may include a moving chessboard, which is shown in FIG. 5. The optokinetic stimulus OS is generated simultaneously or directly before a generation of a sequence of magnetic resonance images BD from the patient P, such that a reaction of the patient P, in particular a movement of the optic nerves ON of the patient P is recorded on the magnetic resonance images BD.

In step 1.II, the mentioned sequence of magnetic resonance images BD using a dynamic Cine magnetic resonance imaging pulse sequence is generated from a brain of a patient P. Vividly spoken, a video of a sectional view of the head of the patient P is generated. As sectional view in a transversal plane relative to the longitudinal axis of the body of the patient P is used which is positioned at the height position of the eyes of the patient P such that in addition to the brain, also a sectional view of the eyes of the patient P is shown in the medical images BD. Such a sectional view is illustrated in FIG. 5 to FIG. 9. To each of these recorded medical images BD, a time stamp TS is assigned which indicates the time at which the medical image has been recorded.

In step 1.III, an amount A-DP of a displacement of the optic nerves ON is measured based on an AI-based displacement determination process. In an exemplary embodiment, a type of characteristic movement may be determined based on the determined amount of displacement of the optic nerve (ON). The eye movement determination device 10 (FIG. 12) may be adapted or configured to generate one or more electronic signals representing the determined type of characteristic movement and/or one or more other determined values, data, and/or information, and provide the electronic signal(s) as an output of the device.

In step 1.IV, it is determined if a w to a vertigo phenomenon is detected based on the determined amount A-DP of displacement of the optic nerve ON and the velocity with which this displacement of the optic nerve was achieved. Based on the determination of such a nystagmus a vestibular migraine is enabled to be diagnosed.

Figure 2:
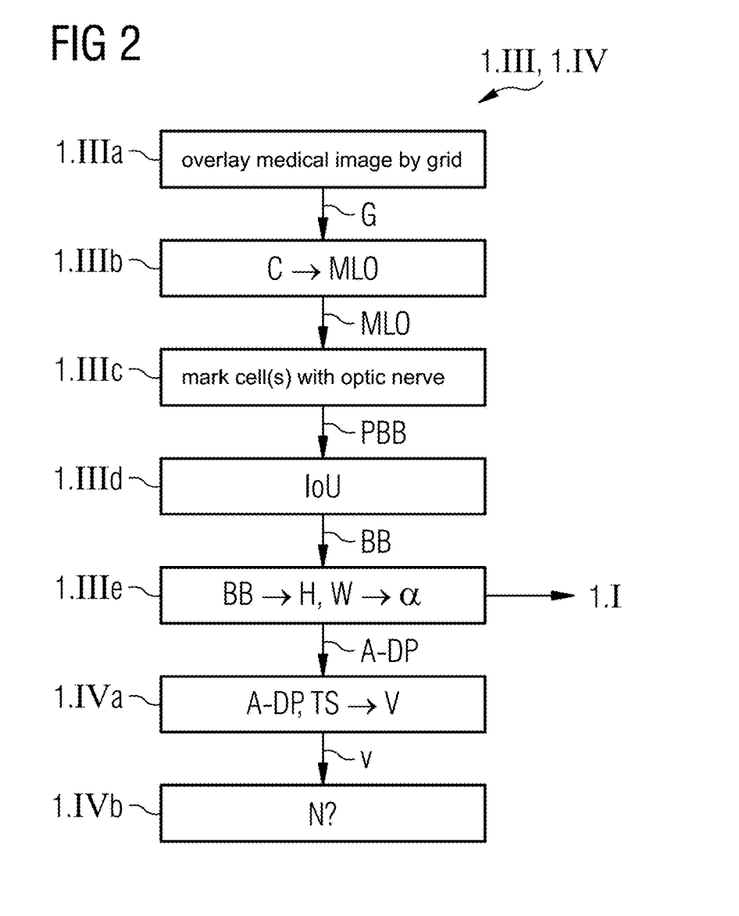
FIG. 2 shows a flowchart diagram illustrating details of step 1.III and 1.IV of the method for determining a type of a characteristic eye movement of a patient shown in FIG. 1, according to an exemplary embodiment of the disclosure.

In FIG. 2, a flow chart diagram depicting details of step 1.III and 1.IV of the method for determining a characteristic eye movement of a patient shown in FIG. 1 is illustrated.

Figure 9:
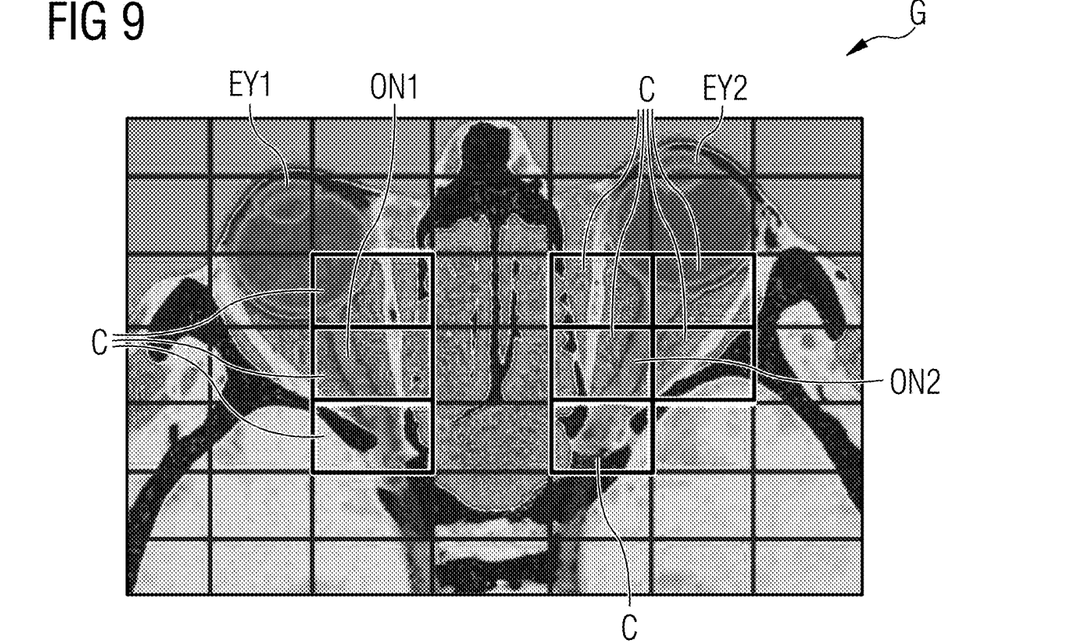
FIG. 9 shows a schematic sectional view onto a brain and the eyes of a patient and a grid laid over the sectional view, according to an exemplary embodiment of the disclosure.

In step 1.IIIa, a medical image BD recorded in step 1.I, is overlayed by a grid G. Such a grid G may include cells C of equal dimension (7*7) as shown in FIG. 9.

In step 1.IIIb, the most likely object MLO within each cell C of the grid G is detected, i.e. it is determined in which cell at least a part of the optic nerve ON is localized. For detecting and localizing the optic nerves ON reliably and quickly, a YOLO algorithm is used.

In step 1.IIIc, each cell in which the optic nerve ON is detected is marked by a part bounding box PBB.

In step 1.IIId, an Intersection over Union IoU metric is used for creating a unified single bounding box BB. Hence, the part bounding boxes PBB are unified to form together for each optic nerve ON a single overall bounding box.

In step 1.IIIe, an angel α representing the orientation of the detected optic nerve ON is calculated based on the height H and width W of the bounding box BB. Then, based on the detected angle α, the amount A-DP of displacement of the optic nerve ON is determined based on the calculated angle α.

Further, the method returns to step 1.I for recording additional medical images BD from the head of the patient P and assigning to each of these medical images BD and to the related amount of displacement A-DP a time stamp TS.

Then, in step 1.IVa, a velocity v of the eye movement of the patient P is calculated based on each determined amount of displacement A-DP and each time stamp TS of each of the medical images BD.

In step 1.IVb, it is determined based on the calculated velocity v of the patient's eyes if the patient P suffers from a vertigo caused nystagmus N or not.

Figure 3:
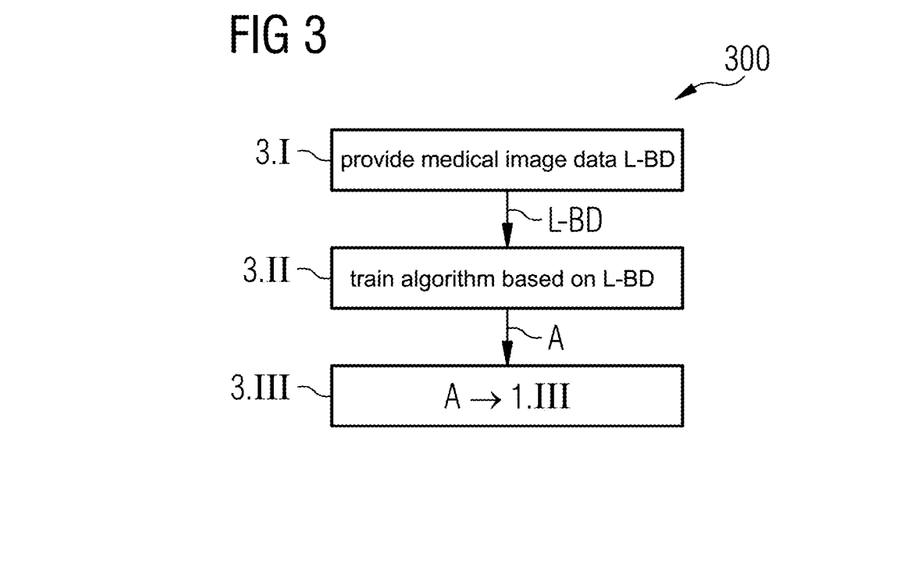
FIG. 3 shows a flowchart diagram illustrating a method for training an AI-based algorithm for determining an amount of a displacement of an optic nerve of a patient according to an exemplary embodiment of the disclosure.

In FIG. 3, a flow chart is shown illustrating a method for training an AI-based algorithm A for determining an amount A-DP of a displacement of an optic nerve ON of a patient P based on at least one medical image BD. The algorithm A can be used for performing step 1.III illustrated in FIG. 1 and FIG. 2. Such a training method is performed before the algorithm A is used in step 1.III of the method for determining a type of a characteristic eye movement of a patient P.

In step 3.I, labelled medical image data L-BD comprising an optic nerve ON of a patient P are received. These labelled medical image data L-BD comprise a dataset with two different sets S1, S2 of medical images, a first training set S1 with medical images BD related to a patient P with regular eye movement and a second training set S2 with medical images BD of patients P with a specified type of characteristic eye movements to be determined. The specified type of characteristic eye movement differs from the regular eye movement and may be related to a specified physiological state, in particular to a disease like vestibular migraine. Such labelled medical image data L-BD are symbolized in the table T shown in FIG. 4. Labelled medical image data L-BD means that the images comprise correct results as reference results. These reference results can be compared with results generated by the algorithm to be trained based on the labelled medical image data L-BD. Based on the comparison, the architecture of the algorithm can be modified such that the results of the algorithm are brought closer to the reference results related to the training data, i.e. the labelled medical image data L-BD. In that case, reference results comprise bounding boxes BB related to optical nerves and the dimensions of these bounding boxes, further also an angle α related to the bounding boxes BB and a velocity v of eye movement calculated based on a sequence of a plurality of medical images.

In step 3.II, the algorithm is trained based on the labelled medical image data L-BD. Such a "training" includes the step of feeding the algorithm A to be trained, including a modifiable algorithm architecture, for example an artificial neural network, with the labelled medical image data L-BD and modify the algorithm architecture based on a comparison between the result generated by the algorithm A and the above-mentioned reference results.

In step 3.III, the trained algorithm A is provided for performing step 1.III illustrated in FIG. 1 and FIG. 2.

Figure 4:
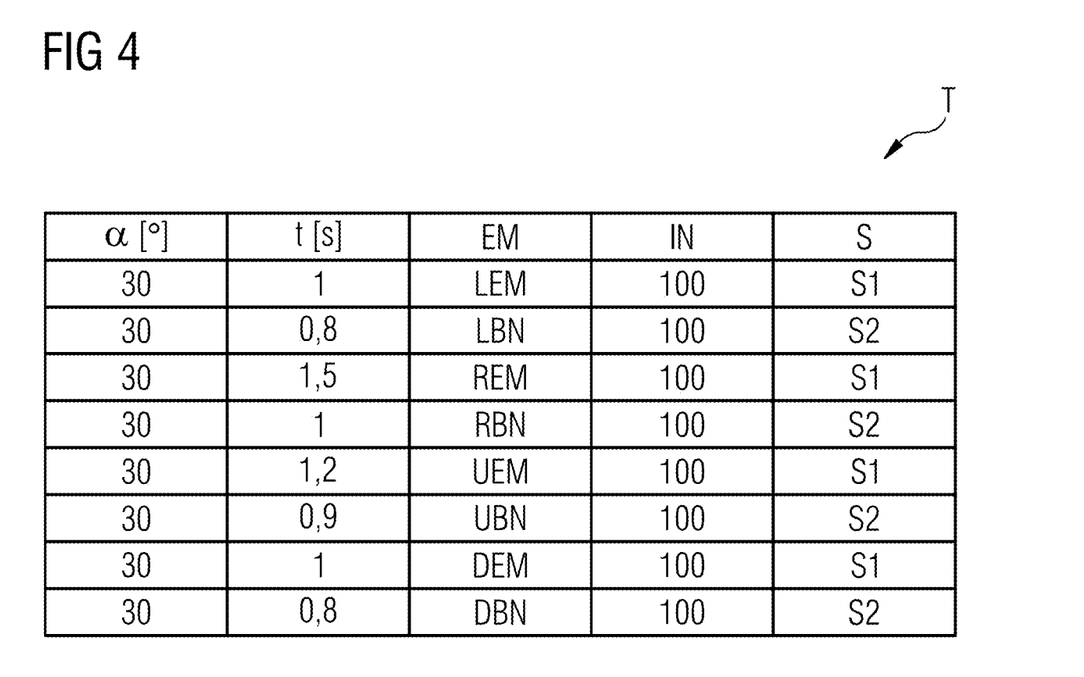
FIG. 4 shows a table showing parameter values of labelled medical image data used for training the AI-based algorithm, according to an exemplary embodiment of the disclosure.

In FIG. 4, a table T, illustrating sets S of different data sets S1, S2 used for the training method of an algorithm shown in FIG. 3 is depicted. As mentioned above, such different data sets S1, S2 include a first training set S1 with medical images BD related to patients P with regular eye movement and a second training set S2 with medical images BD of patients P with a specified type of characteristic eye movement to be determined, in that special case a nystagmus stimulated by an optokinetic stimulus. As mentioned-above, the detection of such a nystagmus is an indicator for vertigo related to vestibular migraines.

The table T shows reference data, which are used for labelling these training data sets S1, S2. In the first column, an angle α of the detected eye movement is represented. The movement angle α of the recorded movement of the eyes of a patient P is always 30° for both sets S1, S2 and all images of these sets, since the optokinetic stimulus used for each patient P is related to a movement of 30°. In the second column of the table T, the time t (in seconds s) which is needed for completing the recorded eye movement of the patient P is displayed. Further, for each type of an optokinetic stimulus OS, in neighbored lines of table T, times t related to the first set S1 and times t related to the corresponding second set S2 are shown as it is indicated by the fifth column. As can be taken from the table T, the values of times t for the regular eye movement stored in the first set S1 is longer than the time of the second set S2, which corresponds to the same optokinetic stimulus. In the third column, the eye movements EM related to different optokinetic stimuli and to the sets S1, S2 are depicted. As can be taken from the table T, related to the first set S1 regular eye movements to the left LEM, to the right REM, up UEM and down DEM are shown. Further corresponding characteristic types of eye movements i.e. a left beating nystagmus LBN, a right beating nystagmus RBN, an up beating nystagmus UBN and a down beating nystagmus DBN are shown in the table T represented by the second training set S2. In the fourth column, the number IN of images or image sequences, i.e. 100 images or sequences of images, corresponding to these different types of eye movements are depicted.

In FIG. 5, a moving chessboard MC used as optokinetic stimulus for the eyes of a patient, is shown. In the lower right corner of FIG. 3, the eyeballs E of the patient are shown, wherein each of the eyeballs E is directed to a different direction which may be a sign of a nystagmus caused by vertigo.

Figure 6:
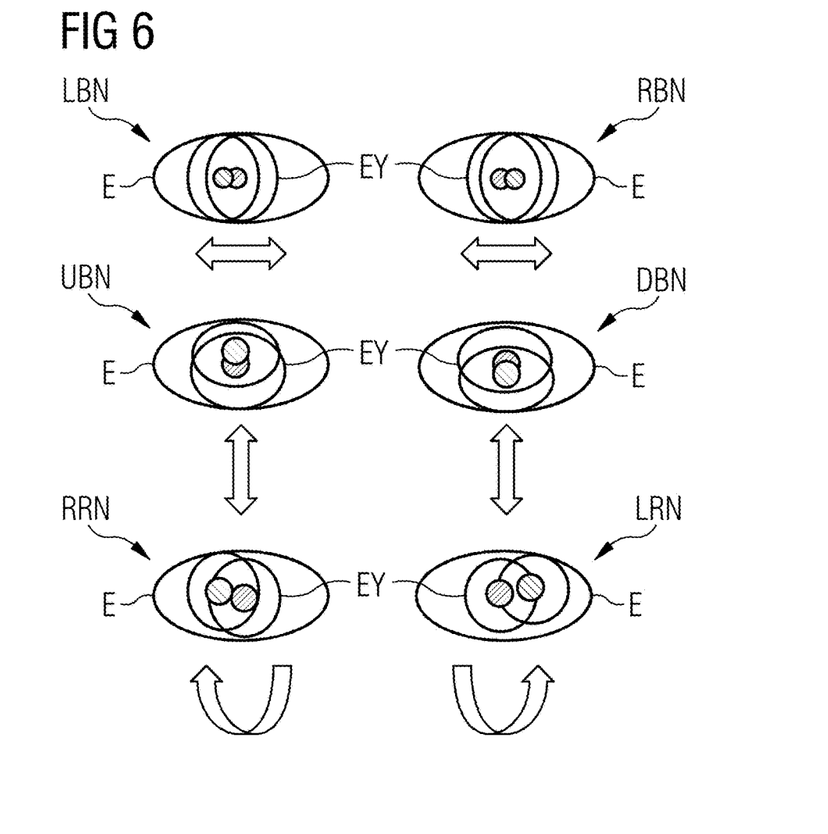
FIG. 6 shows a schematic illustration of a nystagmus movement of the eyes of a patient in different directions, according to an exemplary embodiment of the disclosure.

In FIG. 6, a schematic illustration of different types of a nystagmus movement of the eyes E of a patient P in different directions is depicted. In the first line, a horizontal nystagmus is illustrated, wherein there is a horizontal difference between the positions of the centers of the eyes E of the patient which means that a movement of the eyeballs in the horizontal direction is shown. The pupil with the sparser dashing (from left up to right down) symbolizes the displaced eyeball EY and the pupil with the denser dashing (from left down to right up) symbolizes the original position of the eyeball EY. On the left side of the first line, a left beating nystagmus LBN is shown, wherein the direction of the view of the eye E is displaced to the left side. On the right side of the first line, a right-beating nystagmus RBN is shown, wherein the direction of the view of the eye E is displaced to the right side.

In the second line, there is a vertical Nystagmus shown, wherein there is a vertical difference between the positions of the centers of the eyes E of the patient. On the left side of the second line, an up-beating nystagmus UBN is shown and on the right side of the second line, a down-beating nystagmus DBN is shown. In the lower line of FIG. 6, a rotary nystagmus is illustrated, wherein there is a diagonal difference between the eyeballs EY of the patient. On the left side of the third line, a right rotating nystagmus RRN is shown and on the right side of the third line, a left rotating nystagmus LRN is shown.

Figure 7:
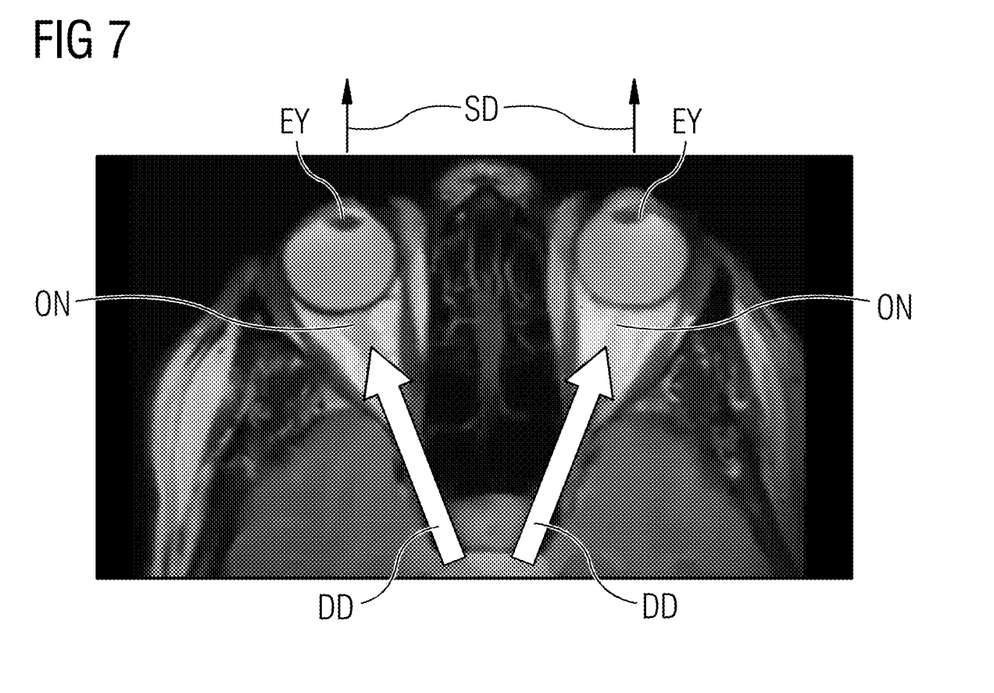
FIG. 7 shows a schematic sectional view onto a brain and the eyes of a patient looking straight at the center, according to an exemplary embodiment of the disclosure.

In FIG. 7, a schematic sectional view onto a brain and the eyeballs EY of patient is illustrated. As can be taken from FIG. 7, the eyeballs EY of the patient are both directed in a straight direction SD and the optic nerves ON are directed in a divergent direction DD.

Figure 8:
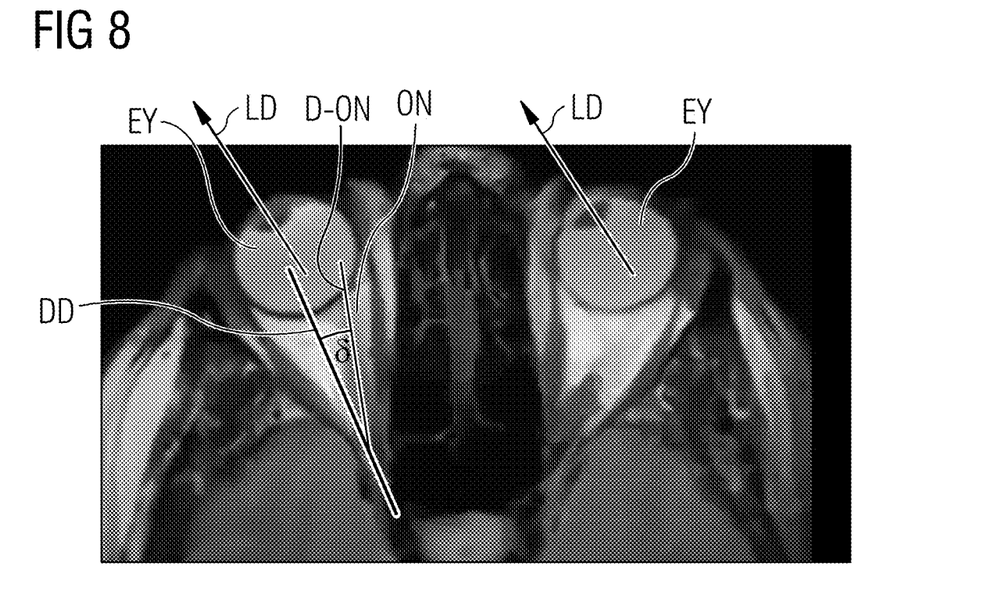
FIG. 8 shows a schematic sectional view onto a brain and the eyes of a patient with a left beating nystagmus while viewing optokinetic stimuli, according to an exemplary embodiment of the disclosure.

In FIG. 8, a schematic sectional view onto a brain and the eyeballs EY of a patient, wherein the eyeballs EY are turned to the left side, is illustrated. In FIG. 8, a displacement D-ON of the optic nerve ON, in particular of the left eye EY compared to FIG. 7 is shown. The displacement D-ON is represented by the angle δ. The angle δ is defined by the different, i.e. divergent directions DD, D-ON of the optic nerve ON in the straight view direction SD of the eyes as shown FIG. 6 and the view direction LD to the left as shown in FIG. 7.

In FIG. 9, a schematic sectional view onto a brain and the eyeballs EY of a patient and a grid G laid over the sectional view are depicted. The cells C of the grid G, including the optic nerve ON1, ON2 of the left eye EY1 and the right eye EY2 are marked. As you can take from FIG. 9, the optic nerve ON1 of the left eye only includes three cells C and the optic nerve ON2 of the right eye includes five cells C. For achieving an overall bounding box for each optic nerve ON1, ON2, first, in each cell C including a part of an optic nerve ON1, ON2, an elementary bounding box is marked.

Figure 10:
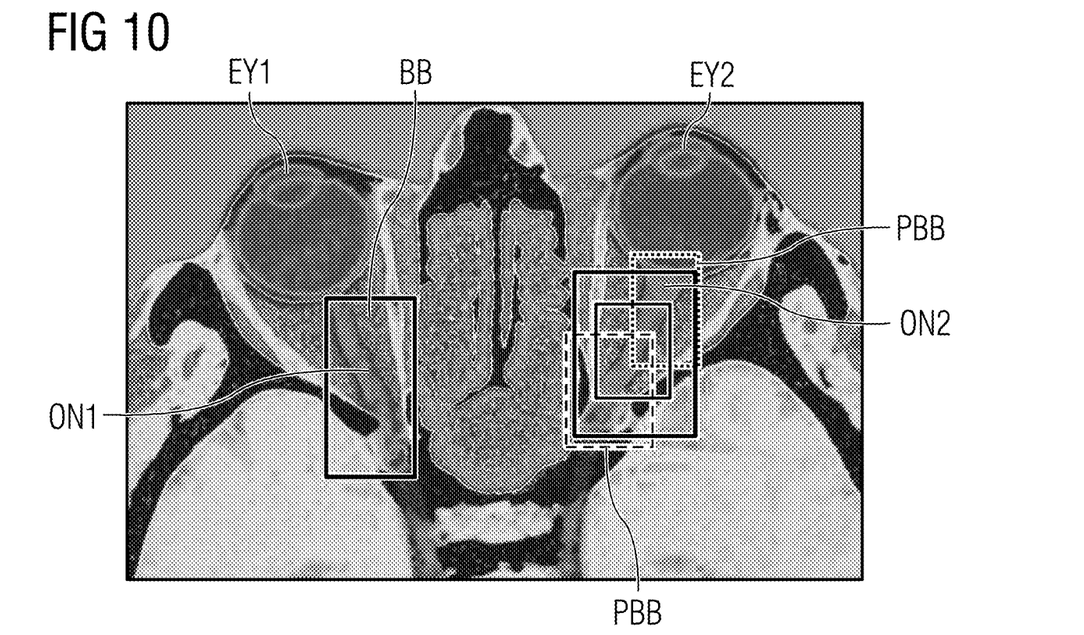
FIG. 10 shows a plurality of bounding boxes for each cell of the grid shown in FIG. 9 that contains the optic nerve, according to an exemplary embodiment of the disclosure.

In FIG. 10, for the right eye EY2, a plurality of part bounding boxes PBB for each cell C of the grid G and expanding from each cell C of the grid G shown in FIG. 9 which contains the right optic nerve ON2 are illustrated. In contrast thereto, for the left eye EY1, these bounding boxes PBB have been replaced by an overall bounding box BB. The part bounding boxes PBB and the overall bounding box BB are generated based on "Intersection over Union" (IoU).

Figure 11:
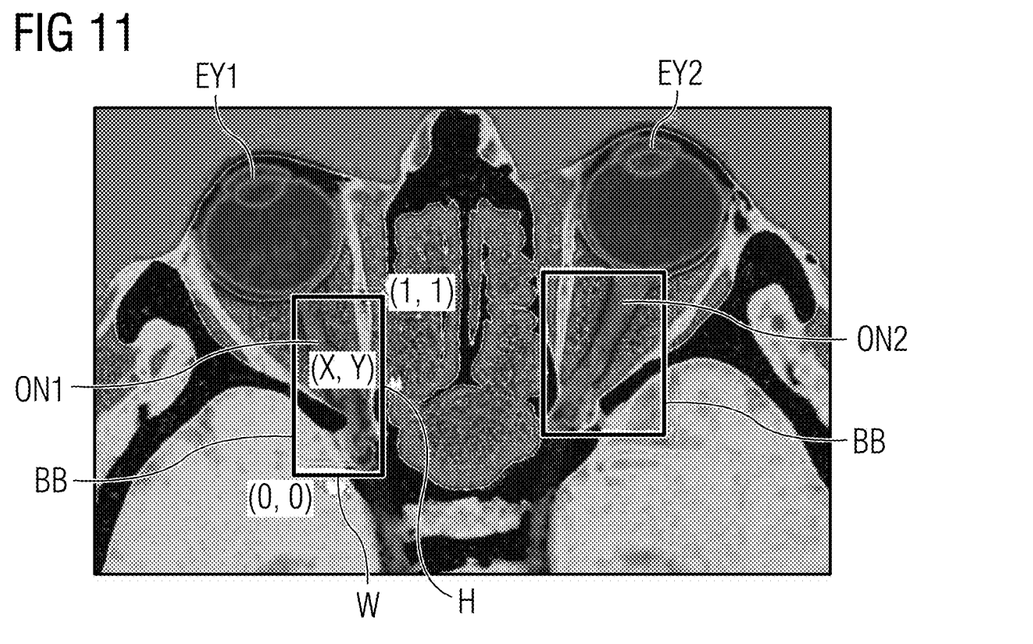
FIG. 11 shows two fused bounding boxes, each related to a single optic nerve, according to an exemplary embodiment of the disclosure.

In FIG. 11, two fused bounding boxes, each related to a single optic nerve, are shown. In FIG. 11, also the width W and the height H of the bounding box BB of the left eye EY1 are indicated. Further, a coordinate system (x, y) including an origin (0,0) in the lower left corner of the bounding box BB of the left eye EY1 and a point (1,1) in the upper right corner of the bounding box BB of the left eye EY1 are depicted.

Figure 12:
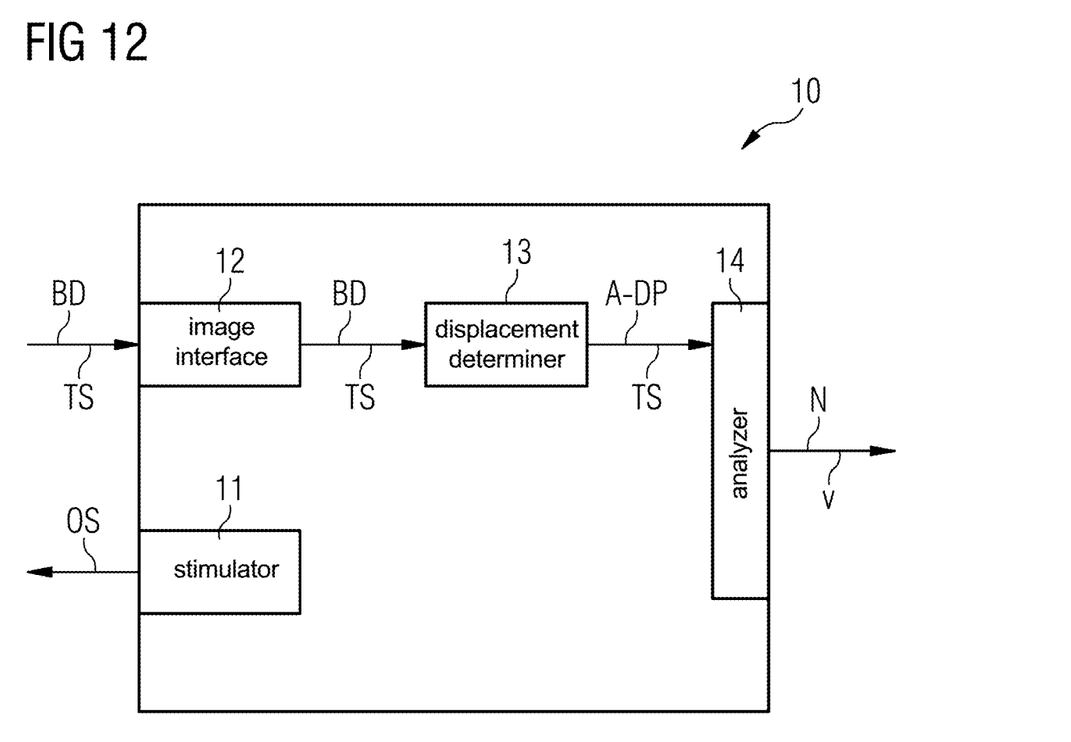
FIG. 12 shows a schematic illustration of an eye movement determination device according to an exemplary embodiment of the disclosure.

In FIG. 12, a schematic illustration of an eye movement determination device (also referred to herein as an eye movement determiner or eye movement determination circuitry) 10 according to an embodiment of the disclosure is illustrated. In an exemplary embodiment, the eye movement determination device 10 (and/or one or more components therein) includes processing circuitry that is configured to perform one or more functions or operations of the eye movement determination device and/or one or more respective functions or operations the respective component(s) therein.

The eye movement determination device 10 includes a stimulation unit (also referred to herein as a stimulator or stimulator circuitry) 11 adapted or configured to provide a patient P (shown in FIG. 13) with an optokinetic stimulus OS for a nystagmus. In an exemplary embodiment, the stimulation unit 11 may be adapted or configured to generate one or more electronic signals representing the stimulus and/or one or more other values, data, and/or information, and provide the electronic signal(s) as an output of the stimulation unit 11 (and/or of device 10).

Further, the eye movement determination device 10 comprises an image interface unit (also referred to image interface or image interface circuitry) 12 adapted or configured to receive a medical image BD of the brain of a patient P and a time stamp TS assigned to each medical image BD from a reconstruction unit or a scan unit of a medical imaging system (not shown in FIG. 12).

Part of the eye movement determination device 10 is also a displacement determination unit (also referred to herein as a displacement determiner or displacement determination circuitry) 13 adapted or configured to determine an amount A-DP of a displacement of the optic nerves ON of the eyes of a patient based on the medical image BD. In an exemplary embodiment, the eye movement determination device 10 may be adapted or configured to use one or more AI-based algorithms or models to determine the amount A-DP of a displacement of the optic nerves ON of the eyes of a patient based on the medical image BD.

The eye movement determination device 10 also comprises an analysis unit (also referred to herein as an analyzer or analyzer circuitry) 14 adapted or configured to determine if a nystagmus is detected based on the determined amount A-DP of displacement of the optic nerve ON and of what type the detected nystagmus is. For example, the velocity v of the eye movement related to the nystagmus is determined and based on the value of the velocity v, it is determined if the eye movement is related to a special physiological phenomenon like a nystagmus N caused by vestibular migraine. In an exemplary embodiment, the analyzer 14 may be adapted or configured to generate one or more electronic signals representing the determination and/or one or more other determined values, data, and/or information, and provide the electronic signal(s) as an output of the analyzer 14 (and/or of device 10).

Figure 13:
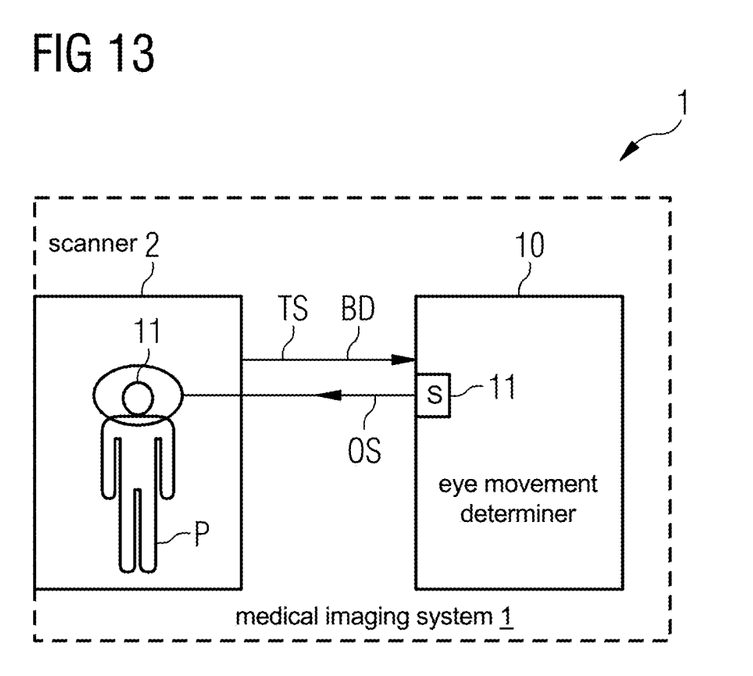
FIG. 13 shows a schematic illustration of a medical imaging system according to an exemplary embodiment of the disclosure.

In FIG. 13, a schematic illustration of a medical imaging system 1 according to an embodiment of the disclosure is represented. The medical imaging system 1 comprises a scan unit (scanner) 2, in which medical images BD are recorded from a patient P. The medical imaging system 1 also comprises a stimulation unit (also referred to herein as a stimulator or stimulator circuitry) 11. The stimulation unit 11 may be adapted or configured to generate an optokinetic stimulus OS for stimulating an eye movement of the patient P, for example a moving chessboard MC (shown in FIG. 5) and applies the optokinetic stimulus OS to the patient P. Part of the medical imaging system 1 is also an eye movement determination device 10 as it is shown in FIG. 12. In an exemplary embodiment, the eye movement determination device 10 may be configured to control the operation of the scanner 2, and may be referred to as controller 10.

The above descriptions are merely exemplary embodiments of the present disclosure, but not intended to limit the present disclosure, and any modifications, equivalent replacements, improvements, etc. made within the spirit and principle of the present disclosure should be included within the scope of protection of the present disclosure.

Further, the use of the undefined article "a" or "one" does not exclude that the referred features can also be present several times. Likewise, the term "unit" or "device" does not exclude that it consists of several components, which may also be spatially distributed.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," or "devices." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, units, or devices, as applicable and relevant, may alternatively be referred to herein as "circuitry," "controllers," "processors," or "processing circuitry," or alternatively as noted herein.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for determining a type of characteristic eye movement of a patient, comprising:
providing the patient with an optokinetic stimulus for stimulating the characteristic eye movement,
generating at least one medical image of the brain of the patient also including the eyes of the patient,
determining an amount of a displacement of an optic nerve of the patient based on the at least one medical image using artificial intelligence (AI) by segmenting the optic nerve in the medical image via a detection that is performed in accordance with a "You Only Look Once" (YOLO) algorithm, and
determining a type of characteristic movement based on the determined amount of displacement of the optic nerve.

2. The method according to claim 1, wherein segmenting the optic nerve comprises:
splitting the medical image into a grid including a plurality of cells,
detecting the most likely object within each cell of the grid,
marking each cell in which the optic nerve is detected by a bounding box, and
using "Intersection over Union" (IoU) for creating a unified single bounding box of the detected optic nerve.

3. The method according to claim 2, wherein:
an angle of the orientation of the detected optic nerve is calculated based on the height and width of the unified single bounding box, and
the amount of a displacement of the optic nerve is determined based on the calculated angle.

4. The method according to claim 1, wherein:
the optokinetic stimulus is adapted to stimulate a nystagmus movement of the patient in case the patient suffers from vestibular migraine, and
the type of characteristic movement comprises a nystagmus movement of the patient's eyes.

5. The method according to claim 1, wherein the optokinetic stimulus comprises a movement of an object in a predetermined direction.

6. The method according to claim 1, wherein the at least one medical image comprises a series of medical images.

7. The method according to claim 6, wherein:
a velocity of an eye movement is determined based on the amount of displacement and a time stamp of each of the series of medical images, and the type of characteristic eye movement of the patient is detected based on the determined velocity.

8. A method for training an artificial intelligence based algorithm for determining an amount of a displacement of an optic nerve of a patient based on at least one medical image, comprising:

receiving labelled medical image data comprising an optic nerve of a patient, wherein the labelled medical image data comprise a dataset with two different sets of medical images comprising a first training set with medical images related to a patient with regular eye movement and a second training set with medical images of patients with a type of characteristic eye movement to be determined;

training the algorithm based on the labelled medical image data; and providing the trained algorithm for determining an amount of a displacement of an optic nerve of a patient based on the at least one medical image.

9. A non-transitory computer-readable storage medium with an executable program stored thereon, that when executed, instructs a processor to perform the method of claim 1.

10. A non-transitory computer-readable storage medium with an executable program stored thereon, that when executed, instructs a processor to perform the method of claim 8.

* * * * *